United States Patent [19]

Clark et al.

[11] 4,029,804
[45] June 14, 1977

[54] INJECTABLE AMOXYCILLIN COMPOSITIONS

[75] Inventors: Dennis Edward Clark, Basking Ridge; Robert Charles Blyth, North Plainfield, both of N.J.

[73] Assignee: Beecham Group Limited, England

[22] Filed: Sept. 22, 1975

[21] Appl. No.: 615,239

[30] Foreign Application Priority Data

Oct. 10, 1974 United Kingdom ............ 43924/74

[52] U.S. Cl. ............................................. 424/271
[51] Int. Cl.$^2$ ...................................... A61K 31/43
[58] Field of Search .................................... 424/271

[56] References Cited
UNITED STATES PATENTS 3,674,776 7/1972 Long et al. .................... 424/271 X Primary Examiner—Albert T. Meyers
Assistant Examiner—Daren M. Stephens

[57] ABSTRACT

Injectable amoxycillin solutions of enhanced stability comprising a water-soluble salt of amoxycillin such as sodium amoxycillin dissolved in a sterile mixture of water and at least one water-miscible pharmaceutically acceptable alcoholic compound preferably including ethanol. A two-part container or syringe is used of which one part contains a predetermined amount of amoxycillin in dry powder form and the second part contains a predetermined amount of a sterile mixture of water and the alcoholic compound.

1 Claim, No Drawings

INJECTABLE AMOXYCILLIN COMPOSITIONS

This invention concerns improvements in and relating to amoxycillin. Amoxycillin is the generic name for the penicillin, 6-[D(-)-α-amino-p-hydroxyphenylacetamido]-penicillanic acid which can also be called D-(-)-α-amino- p-hydroxybenzylpenicillin. It has the structural formula

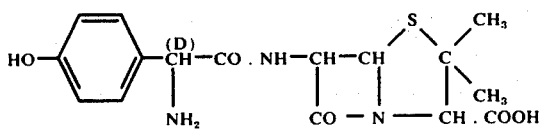

Amoxycillin is described in British Pat. No. 1,241,844 and U.S. Pat. No. 3,674,776. Amoxycillin has found widespread clinical application because it is a penicillin with a broad spectrum of activity against both gram-positive and gram-negative bacteria and high blood levels of the antibiotic are achieved after oral administration.

It is desirable that any antibiotic should be made available in a form suitable for administration by injection, as well as for oral administration. It has now been found that injectable solutions of the sodium salt of amoxycillin possess an enhanced stability if the solvent used for reconstitution is a mixture of water and at least one alcoholic compound. Such solutions can give favourable blood levels on injection.

The improved stability of the new solution may be seen from the considerable reduction in loss of antibiotic potency on storage of the solution at room temperature. For example, a solution of freeze-dried sodium amoxycillin dissolved in water at the concentration normally employed for intra-muscular injection (250 mg/ml.) can lose up to 20% potency in 1 hour at room temperature, whereas the potency loss in this time is only 10% when the solvent is 25% ethanol-water. This increased stability is a surprising discovery since the same effect is not obtained with solutions of sodium ampicillin. A solution of sodium ampicillin in water or in 25% ethanol-water is found to lose about 5% of its antibiotic potency on storage for 1 hour at room temperature. In making use of this discovery of the enhanced stability of sodium amoxycillin in aqueous-alcoholic solutions, the alcohol in the reconstitution solvent must of course, be miscilbe with water and pharmaceutically acceptable. The amoxycillin salt will normally be prepared as a dry powder suitable for dissolution shortly before use and the present discovery also suggests that such powder should be supplied in association with a container of appropriate aqueous-alcoholic solvent for dissolution of the salt. In this way, the proportion of solvent to salt and the precise proportion of alcohol to water in the solvent can more closely be controlled.

Accordingly, from one aspect, the invention provides a solution adapted for injection which comprises the sodium salt of amoxycillin dissolved in a sterile mixture of water and at least one water-miscible pharmaceutically acceptable alcoholic compound.

Suitable pharmaceutically acceptable alcoholic compounds may be selected from ethanol, n-propanol, iso-propanol, diethylene glycol, propylene glycol and glyceraldehyde. Normally, not more than three and preferably not more than two such compounds will be included in the mixed solvent system used in this invention. Normally, ethanol will be one of the components of the mixed solvent system.

Preferably, the mixed solvent system will contain 35 - 85% v/v of water and will frequently contain 45 - 75% v/v of water.

From a second aspect, the invention provides a two-pack container or two-part syringe wherein one pack or part contains a predetermined quantity of the sodium salt of amoxycillin in the form of a dry powder and the second pack or part contains a predetermined quantity of a mixture of water and at least one water-miscible pharmaceutically acceptable alcoholic compound.

The amoxycillin salt will initially be formed as a dry powder. For example, a suspension or solution of amoxycillin in an appropriate solvent may be treated with sodium hydroxide, sodium carbonate or sodium bicarbonate to produce an aqueous solution of sodium amoxycillin. The amount of alkali used will be about 1.0 mole. A slight excess is often required to obtain complete dissolution but this should be kept to a minimum as excess alkali causes rapid degradation of the penicillin and unacceptably high pH levels. This solution may then be conveniently reduced to a powder in conventional manner by percipitation, freeze-drying or spray-drying. Freeze-drying can be a particularly useful method of obtaining the powdered salt.

If desired, such freeze-drying or spray-drying may be carried out in an aqueous solution of the amoxycillin containing 10 to 25% of ethanol. Generally, the solutions used for drying should contain 5 to 50% and preferably 10 - 20% of sodium amoxycillin in order to minimise degradation thereof during the drying process. Alternatively, the sodium amoxycillin may be precipitated from a solution in an inert organic solvent of a conventional tertiary amine salt of amoxycillin using a conventional precipitant such as an alkali-metal alkoxide or salt of a carboxylic acid such as sodium ethylhexoate.

For the purposes of the invention, the sodium salt of amoxycillin is dissolved in a mixture of water and at least one water-miscible pharmaceutically acceptable alcoholic compound. Such a mixture must be sterile. The water employed should be in accordance with the definitions of 'water for injection' as described in U.S. Pharmacopoeia XVIII, p. 777 or the British Pharmacopoeia, 1973, p. 500.

An alternative way of carrying out the present invention uses the amoxycillin in the free amino acid from, either as a specific hydrate e.g. trihydrate, or otherwise, and the desired soluble amoxycillin salt is then formed in situ in the injectable solution of the invention by reconstituting the amoxycillin with the aforementioned aqueous alcohol mixtures but also containing about one equivalent of a basic sodium salt.

Accordingly, from a third aspect, the invention provides a two-pack container or two-part syringe wherein one pack or part contains a predetermined quantity of amoxycillin in a solid form, and the second part contains a predetermined quantity of a mixture of water and at least one water-miscible pharmaceutically acceptable alcohol and dissolved therein substantially one equivalent of alkali.

In this third aspect of the invention, the dissolved alkali can be sodium hydroxide, sodium bicarbonate, sodium carbonate, tri sodium phosphate, sodium glycinate or the like. Especially preferred as such alkali is sodium hydroxide, which has a greater solubility in the aforementioned aqueous-alcohol solution.

If desired small quantities of alkali materials such as those used in the third aspect of the invention may also be included in the sterile mixture of water and at least one water-miscible pharmaceutically acceptable alcoholic compound present in the first and second aspects of this invention.

The injectable solution of the invention should normally contain from 5 – 50%, preferably about 20 – 30%, by weight of sodium amoxycillin, that is, from about 50 – 500mg. preferably about 250mg. of amoxycillin per ml. of solvent. Normally, each injectable dose of amoxycillin salt should contain from 125mg. to 5g. thereof. The aforesaid twin-pack or two-part syringe normally comprises one unit containing such quantity of the penicillin and the other unit should contain from 0.25ml. – 20ml. of the aforesaid mixed solvent which if desired contains an alkali as herebefore indicated.

The invention is illustrated by the following Examples which also indicate the enhanced stability of the amoxycillin salt solutions as compared to those wherein the amoxycillin salt is merely dissolved in water.

EXAMPLE 1

Varying quantities of amoxycillin trihydrate were slurried in water and water-ethanol (75:25). To the slurry was added, drop-wise, 2N-sodium hydroxide until the amoxycillin trihydrate dissolved and produced solutions of 5–35% sodium amoxycillin on a free acid basis. The solutions were allowed to remain at room temperature (22° C) for 1 hour and their potencies determined by the hydroxylamine assay method. The concentrations, sodium hydroxide equivalents required, and retained potencies recorded below, show that markedly large excesses of alkali are needed for dissolution in water and the stability of sodium amoxycillin in ethanol/water (25:75) is significantly greater than in water at all concentrations tested.

| Conc. % w/v | Aqueous Min. Equiv. NaOH | EtOH—H$_2$O Min. Equiv. NaOH | Aqueous % Ret. Potency | EtOH—H$_2$O % Ret. Potency |
|---|---|---|---|---|
| 5  | 1.00 | 0.97 | 100 | 100 |
| 10 | 1.07 | 1.00 | 96  | 96  |
| 15 | 1.09 | 1.01 | 84  | 92  |
| 20 | 1.09 | 1.03 | 80  | 93  |
| 25 | 1.10 | 1.03 | 75  | 90  |

EXAMPLE 2

Experiments carried out as in Example 1 except the temperature of dissolution and the standing period was maintained at 15° C.

| Conc. % w/v | Aqueous Min. Equiv. NaOH | EtOH—H$_2$O Min. Equiv. NaOH | Aqueous % Ret. Potency | EtOH—H$_2$O % Ret. Potency |
|---|---|---|---|---|
| 5  | 1.06 | 0.94 | 96 | 97 |
| 10 | 1.11 | 0.99 | 92 | 95 |
| 15 | 1.13 | 1.01 | 86 | 94 |
| 20 | 1.16 | 1.02 | 86 | 93 |
| 25 | 1.15 | 1.01 | 80 | 90 |

EXAMPLE 3

Experiments carried out as in Example 1 except the temperature of dissolution and the holding period were 0.5° C.

| Conc. % w/v | Aqueous Min. Equiv. NaOH | EtOH—H$_2$O Min. Equiv. NaOH | Aqueous % Ret. Potency | EtOH—H$_2$O % Ret. Potency |
|---|---|---|---|---|
| 5  | 1.11 | 1.00 | 92 | 95 |
| 10 | 1.22 | 1.08 | 90 | 95 |
| 15 | 1.27 | 1.11 | 88 | 95 |
| 20 | 1.26 | 1.08 | 87 | 94 |
| 25 | 1.27 | 1.10 | 88 | 95 |

EXAMPLE 4

Sodium amoxycillin with varying amounts of sodium hydroxide was reconstituted in water at 25% w/v concentration (free acid basis). Only after 1.12 equivalents of sodium hydroxide was added did the sodium amoxycillin dissolve. The data are recorded below.

| Time Mins. | Sodium Hydroxide Used (Equivalent) | | | | |
|---|---|---|---|---|---|
|    | 0.97 | 1.00 | 1.04 | 1.07 | 1.12 |
| 15 | N.S.* | N.S. | N.S. | N.S. | 92 |
| 30 | N.S.  | N.S. | N.S. | N.S. | 87 |
| 45 | N.S.  | N.S. | N.S. | N.S. | 84 |
| 60 | N.S.  | N.S. | N.S. | N.S. | 81 |

*Not Soluble

EXAMPLE 5

To 5cc vials containing sodium amoxycillin equivalent to 250mg. amoxycillin free acid was added 0.9 ml. ethanol-water (25:75). The potencies were measured initially and after 1 hour at room temperature (22° C). The results are as recorded below.

| Sample No. | A | B | C | D |
|---|---|---|---|---|
| % Retained Potency (1 hour at 22° C) | 92 | 91 | 91 | 91 |

EXAMPLE 6

The reconstitution stability (22° C) of sodium ampicillin (25% w/v as free acid), was measured in water and ethanol/water (25:75). The potencies were determined by the hydroxylamine assay method at intervals up to 3 hours. The results are recorded below.

| Reconstitution Stability of Sodium Ampicillin (25% w/v Free Acid) | | | | |
|---|---|---|---|---|
| Sample No. | A | B | C | D |
| % Retained Potency (1 hour at 22° C) | 92 | 91 | 91 | 91 |

EXAMPLE 6

The reconstitution stability (22° C) of Sodium Ampicillin (25% w/v as free acid) was measured in water and ethanol/water (25:75). The potencies were determined by the hydroxylamine assay method at intervals up to 3 hours. The results are recorded below.

| Reconstitution Stability of Sodium Ampicillin (25% w/v free acid) at 220° C in Water and Ethanol-Water (25:75) | | |
|---|---|---|
| Time Minutes | Water Solution % Retained Potency | Ethanol/Water Solution % Retained Potency |
| 0 | 100 | 100 |
| 30 | 99 | 96 |
| 60 | 96 | 94 |
| 120 | 93 | 94 |
| 180 | 92 | 93 |

EXAMPLE 7

A 6 cc vial containing 289 mg. of Amoxycillin Trihydrate equivalent to 250 mg. of Amoxycillin (0.684 meq.) was reconstituted with 25% ethanol-water (0.9 ml.) containing 0.684 meq. of sodium hydroxide. Rapid dissolution occurred to give a clear solution. Samples were taken at various intervals to 1 hour at room temperature and assayed by the hydroxylamine method.

| Time Minutes | % Retained Potency | % Initial Reconstitution Potency |
|---|---|---|
| 0 | 89 | 100 |
| 15 | 90 | 101 |
| 30 | 89 | 100 |
| 60 | 87 | 100 |

EXAMPLE 8

Favoured twin-packs for use in this invention comprise a vial of sterile sodium amoxycillin and an ampoule or vial for intra-muscular administration. The contents of the ampoules or vials may be as follows:

| Sodium Amoxycillin (Dose Equivalent to mg. Amoxycillin) | Diluent, 25% Aqueous Ethanol (ml.) | Approximate Reconstituted Volume (ml.) |
|---|---|---|
| 125 | 0.4 | 0.5 |
| 250 | 0.9 | 1.0 |
| 500 | 1.8 | 2.0 |
| 1000 | 3.6 | 4.0 |
| 2000 | 7.2 | 8.0 |
| 4000 | 14.4 | 16.0 |

EXAMPLE 9

An experiment was carried out as described in Example 7 except that 0.9 ml. of a solution of sodium hydroxide (0.715 meq.) in 25% isopropanol-water was used to reconstitute the amoxycillin trihydrate. Rapid dissolution occurred to yield a clear solution, which after standing at room temperature for 1 hour retained 93% of the initial reconstitution potency.

| Time Minutes | % Retained Potency | % Initial Reconstitution Potency |
|---|---|---|
| 0 | 96 | 100 |
| 15 | 93 | 97 |
| 30 | 89 | 93 |
| 60 | 89 | 93 |

*Based on potency of Amoxycillin Trihydrate.

EXAMPLE 10

An experiment was performed as described in Example 7 except that 0.9 ml. of a solution of sodium hydroxide (0.691 meq.) in 25% n-propanol-water was used to reconstitute the amoxycillin trihydrate. After a 1 hour stand at room temperature the clear solution had retained 95% of the initial reconstitution potency.

| Time Minutes | % Retained Potency | % Initial Reconstitution Potency |
|---|---|---|
| 0 | 93 | 100 |
| 15 | 93 | 100 |
| 30 | 88 | 95 |
| 60 | 88 | 95 |

What we claim is:
1. A solution adapted for injection which comprises 5–50% by weight of the sodium salt of amoxycillin dissolved in a sterile mixture of water and one or two water-miscible pharmaceutically acceptable alcoholic compounds selected from the group consisting of ethanol, n-propanol, iso-propanol, diethylene glycol, propylene glycol and glyceraldehyde, the mixed solvent system containing 35–85% v/v of water.

* * * * *